United States Patent
Ferree et al.

(10) Patent No.: US 7,201,776 B2
(45) Date of Patent: Apr. 10, 2007

(54) ARTIFICIAL INTERVERTEBRAL DISC REPLACEMENTS WITH ENDPLATES

(76) Inventors: Bret A. Ferree, 1238 Cliff Laine Dr., Cincinnati, OH (US) 45208; David Tompkins, 647 Wallace Ave., Milford, OH (US) 45150

( * ) Notice: Subject to any disclaimer, the term of this patent is extended or adjusted under 35 U.S.C. 154(b) by 613 days.

(21) Appl. No.: 10/303,385

(22) Filed: Nov. 25, 2002

(65) Prior Publication Data

US 2003/0074076 A1 Apr. 17, 2003

Related U.S. Application Data

(63) Continuation-in-part of application No. 10/191,639, filed on Jul. 9, 2002, which is a continuation-in-part of application No. 09/415,382, filed on Oct. 8, 1999, now Pat. No. 6,419,704, and a continuation-in-part of application No. 09/580,231, filed on May 26, 2000, now Pat. No. 6,494,883.

(51) Int. Cl.
*A61F 2/44* (2006.01)

(52) U.S. Cl. ............................................. 623/17.16

(58) Field of Classification Search ... 623/17.11–17.16
See application file for complete search history.

(56) References Cited

U.S. PATENT DOCUMENTS

| | | | |
|---|---|---|---|
| 2,677,369 A | 5/1954 | Knowles | 128/92 |
| 3,366,975 A | 2/1968 | Pangman | 3/36 |
| 3,426,364 A | 2/1969 | Lumb | 3/1 |
| 3,551,560 A | 12/1970 | Thiele | 424/95 |
| 3,593,342 A | 7/1971 | Niebauer | 3/1 |
| 3,648,294 A | 3/1972 | Shahrestani | 3/1 |
| 3,855,638 A | 12/1974 | Pilliar | 3/1 |
| 3,867,728 A | 2/1975 | Stubstad et al. | 3/1 |
| 3,875,595 A | 4/1975 | Froning | 3/1 |
| 3,883,902 A | 5/1975 | Lynch | 3/36 |
| 4,229,839 A | 10/1980 | Schwemmer | 3/1.91 |
| 4,309,777 A | 1/1982 | Patil | 3/1.91 |
| 4,349,921 A | 9/1982 | Kuntz | 3/1 |
| 4,657,550 A | 4/1987 | Daher | 606/61 |
| 4,663,358 A | 5/1987 | Hyon et al. | 521/64 |
| 4,707,872 A | 11/1987 | Hessel | 5/451 |
| 4,714,469 A | 12/1987 | Kenna | 623/17 |
| 4,759,766 A | 7/1988 | Buettner-Janz et al. | 623/17 |
| 4,772,287 A | 9/1988 | Ray et al. | 623/17.11 |
| 4,863,477 A * | 9/1989 | Monson | 623/17.12 |
| 4,874,389 A | 10/1989 | Downey | 623/17 |
| 4,878,915 A | 11/1989 | Brantigan | 623/17 |
| 4,904,260 A | 2/1990 | Ray et al. | 623/17.16 |

(Continued)

*Primary Examiner*—Suzette Gherbi
(74) *Attorney, Agent, or Firm*—Gifford, Krass, Groh, Sprinkle, Anderson & Citkowski, PC

(57) ABSTRACT

An artificial disc replacement (ADR) includes a pair of opposing endplate components, each attached to one of the upper and lower vertebrae, a cushioning component disposed between the endplate components; and a filler material contained within the cushioning component. The filler material may be a gas, liquid, foam, or gel, including a hydrogel. In a preferred embodiment, the ADR may further include one or more opposing, spaced-apart projections configured to impinge if the endplate components are subjected to an excessive force. Such projections may allow for unrestricted motion between the endplates until impingement, or may restrict translation between the endplates until a greater excessive force is reached. One or both of the endplate components may include a modified surface to increase adherence to the respective vertebral endplates.

25 Claims, 3 Drawing Sheets

U.S. PATENT DOCUMENTS

| | | | | |
|---|---|---|---|---|
| 4,911,718 | A | 3/1990 | Lee et al. | 623/17 |
| 4,917,704 | A | 4/1990 | Frey et al. | 623/17 |
| 4,932,969 | A | 6/1990 | Frey et al. | 623/17 |
| 4,946,378 | A | 8/1990 | Hirayama et al. | 623/17 |
| 5,002,576 | A | 3/1991 | Furhmann et al. | 623/17 |
| 5,015,247 | A | 5/1991 | Michelson | 606/61 |
| 5,026,373 | A | 6/1991 | Ray et al. | 606/61 |
| 5,035,716 | A | 7/1991 | Downey | 623/17 |
| 5,047,055 | A | 9/1991 | Bao et al. | 623/17 |
| 5,071,437 | A | 12/1991 | Steffee | 623/17 |
| 5,108,438 | A | 4/1992 | Stone | 623/17 |
| 5,123,926 | A | 6/1992 | Pisharodi | 623/17 |
| 5,171,280 | A | 12/1992 | Baumgartner | 623/17 |
| 5,171,281 | A | 12/1992 | Parsons et al. | 623/17 |
| 5,192,326 | A | 3/1993 | Bao et al. | 606/60 |
| 5,192,327 | A | 3/1993 | Brantigan | 606/60 |
| 5,246,458 | A | 9/1993 | Graham | 623/17 |
| 5,258,031 | A | 11/1993 | Salib et al. | 623/17 |
| 5,258,043 | A | 11/1993 | Stone | 623/66 |
| 5,292,332 | A | 3/1994 | Lee | 606/213 |
| 5,314,477 | A | 5/1994 | Marnay | 623/17 |
| 5,320,644 | A | 6/1994 | Baumgartner | 623/17 |
| 5,336,223 | A | 8/1994 | Rogers | 606/61 |
| 5,370,697 | A | 12/1994 | Baumgartner | 623/17 |
| 5,375,823 | A | 12/1994 | Navas | 267/195 |
| 5,401,269 | A | 3/1995 | Buttner-Janz et al. | 623/17 |
| 5,425,773 | A | 6/1995 | Boyd et al. | 623/17 |
| 5,458,642 | A | 10/1995 | Beer | 623/17 |
| 5,464,421 | A | 11/1995 | Wortrich | 606/213 |
| 5,514,180 | A | 5/1996 | Heggeness et al. | 623/17.11 |
| 5,534,028 | A | 7/1996 | Bao et al. | 623/17 |
| 5,534,030 | A | 7/1996 | Navarro et al. | 623/17 |
| 5,545,229 | A | 8/1996 | Parsons et al. | 623/17 |
| 5,556,431 | A | 9/1996 | Buttner-Jan | 623/17 |
| 5,571,192 | A | 11/1996 | Schonhoffer | 606/61 |
| 5,609,635 | A | 3/1997 | Michelson | 623/17 |
| 5,645,565 | A | 7/1997 | Rudd et al. | 606/213 |
| 5,645,596 | A | 7/1997 | Kim et al. | 623/17 |
| 5,645,597 | A | 7/1997 | Krapiva | 623/17 |
| 5,674,294 | A | 10/1997 | Bainville et al. | 623/17 |
| 5,674,296 | A | 10/1997 | Bryan et al. | 623/17 |
| 5,683,465 | A | 11/1997 | Shinn et al. | 623/17 |
| 5,693,100 | A | 12/1997 | Pisharodi | 623/17.16 |
| 5,702,450 | A | 12/1997 | Bisserie | 623/17 |
| 5,702,455 | A | 12/1997 | Saggar | 623/17.15 |
| 5,711,960 | A | 1/1998 | Shikinami | 424/426 |
| 5,716,416 | A | 2/1998 | Lin | 623/17 |
| 5,800,549 | A | 9/1998 | Bao et al. | 623/17 |
| 5,814,084 | A | 9/1998 | Grivas et al. | 623/23.48 |
| 5,824,093 | A | 10/1998 | Ray et al. | 623/17 |
| 5,824,094 | A | 10/1998 | Serhan et al. | 623/17 |
| 5,865,845 | A | 2/1999 | Thalgott | 623/17 |
| 5,865,846 | A | 2/1999 | Bryan et al. | 623/17 |
| 5,888,226 | A | 3/1999 | Rogozinski | 623/17 |
| 5,893,889 | A | 4/1999 | Harrington | 623/17 |
| 5,899,941 | A | 5/1999 | Nishijima et al. | 623/17 |
| 5,906,616 | A | 5/1999 | Pavlov et al. | 606/61 |
| 5,928,284 | A | 7/1999 | Mehdizadeh | 623/17 |
| 5,964,807 | A | 10/1999 | Gan et al. | 623/17.11 |
| 5,976,186 | A | 11/1999 | Bao et al. | 623/17.16 |
| 6,022,376 | A | 2/2000 | Assell et al. | 623/17.16 |
| 6,045,554 | A | 4/2000 | Grooms et al. | 606/73 |
| 6,090,112 | A | 7/2000 | Zucherman et al. | 606/61 |
| 6,110,210 | A | * 8/2000 | Norton et al. | 623/17.16 |
| 6,113,639 | A | 9/2000 | Ray et al. | 623/17.16 |
| 6,132,465 | A | 10/2000 | Ray et al. | 623/17.16 |
| 6,146,420 | A | 11/2000 | McKay | 623/17.11 |
| 6,187,048 | B1 | 2/2001 | Milner et al. | 623/17.12 |
| 6,200,347 | B1 | 3/2001 | Anderson et al. | 623/11.11 |
| 6,214,050 | B1 | 4/2001 | Huene | 623/17.15 |
| 6,245,072 | B1 | 6/2001 | Zdeblick et al. | 606/61 |
| 6,261,586 | B1 | 7/2001 | McKay | 424/422 |
| 6,270,528 | B1 | 8/2001 | McKay | 623/16.11 |
| 6,375,682 | B1 | * 4/2002 | Fleischmann et al. | 623/17.12 |
| 6,402,785 | B1 | * 6/2002 | Zdeblick et al. | 623/17.16 |
| 6,419,704 | B1 | * 7/2002 | Ferree | 623/17.12 |
| 6,494,883 | B1 | * 12/2002 | Ferree | 606/61 |
| 6,533,818 | B1 | * 3/2003 | Weber et al. | 623/17.16 |
| 2001/0020186 | A1 | 9/2001 | Boyce et al. | 623/17.16 |
| 2001/0034553 | A1 | 10/2001 | Michelson | 623/17.11 |
| 2001/0039458 | A1 | 11/2001 | Boyer II et al. | 623/23.63 |
| 2001/0056302 | A1 | 12/2001 | Boyer II et al. | 623/17.15 |
| 2002/0026244 | A1 | * 2/2002 | Trieu | 623/17.16 |

* cited by examiner

ARTIFICIAL INTERVERTEBRAL DISC REPLACEMENTS WITH ENDPLATES

REFERENCE TO RELATED APPLICATIONS

This application is a continuation-in-part of U.S. patent application Ser. No. 10/191,639, filed Jul. 9, 2002; which is a continuation-in-part of U.S. patent application Ser. No. 09/415,382, filed Oct. 8, 1999, now U.S. Pat. No. 6,419,704, and Ser. No. 09/580,231, filed May 26, 2000 U.S. Pat. No. 6,494,883; the entire content of each application and patent being incorporated herein by reference.

FIELD OF THE INVENTION

This invention relates generally to surgical techniques and prosthetic components therefor and, in particular, to intervertebral disc replacement apparatus and methods of implanting the same.

BACKGROUND OF THE INVENTION

Eighty-five percent of the population will experience low back pain at some point. Fortunately, the majority of people recover from their back pain with a combination of benign neglect, rest, exercise, medication, physical therapy, or chiropractic care. A small percent of the population will suffer chronic low back pain. The cost of treatment of patients with spinal disorders plus the patient's lost productivity is estimated at 25 to 100 billion dollars annually.

Seven cervical (neck), 12 thoracic, and 5 lumbar (low back) vertebrae form the normal human spine. Intervertebral discs reside between adjacent vertebra with two exceptions. First, the articulation between the first two cervical vertebrae does not contain a disc. Second, a disc lies between the last lumbar vertebra and the sacrum (a portion of the pelvis).

The spine supports the body, and protects the spinal cord and nerves. The vertebrae of the spine are also supported by ligaments, tendons, and muscles which allow movement (flexion, extension, lateral bending, and rotation). Motion between vertebrae occurs through the disc and two facet joints. The disc lies in the front or anterior portion of the spine. The facet joints lie laterally on either side of the posterior portion of the spine.

The human intervertebral disc is an oval to kidney bean shaped structure of variable size depending on the location in the spine. The outer portion of the disc is known as the annulus fibrosis. The annulus is formed of 10 to 60 fibrous bands. The fibers in the bands alternate their direction of orientation by 30 degrees between each band. The orientation serves to control vertebral motion (one half of the bands tighten to check motion when the vertebra above or below the disc are turned in either direction).

The annulus contains the nucleus. The nucleus pulpous serves to transmit and dampen axial loads. A high water content (70–80 percent) assists the nucleus in this function. The water content has a diurnal variation. The nucleus imbibes water while a person lies recumbent. Activity squeezes fluid from the disc. Nuclear material removed from the body and placed into water will imbibe water swelling to several times its normal size. The nucleus comprises roughly 50 percent of the entire disc. The nucleus contains cells (chondrocytes and fibrocytes) and proteoglycans (chondroitin sulfate and keratin sulfate). The cell density in the nucleus is on the order of 4,000 cells per micro liter.

Interestingly, the adult disc is the largest avascular structure in the human body. Given the lack of vascularity, the nucleus is not exposed to the body's immune system. Most cells in the nucleus obtain their nutrition and fluid exchange through diffusion from small blood vessels in adjacent vertebra.

The disc changes with aging. As a person ages the water content of the disc falls from approximately 85 percent at birth to 70 percent in the elderly. The ratio of chondroitin sulfate to keratin sulfate decreases with age. The ratio of chondroitin 6 sulfate to chondroitin 4 sulfate increases with age. The distinction between the annulus and the nucleus decreases with age. These changes are known as disc degeneration. Generally disc degeneration is painless.

Premature or accelerated disc degeneration is known as degenerative disc disease. A large portion of patients suffering from chronic low back pain are thought to have this condition. As the disc degenerates, the nucleus and annulus functions are compromised. The nucleus becomes thinner and less able to handle compression loads. The annulus fibers become redundant as the nucleus shrinks. The redundant annular fibers are less effective in controlling vertebral motion. The disc pathology can result in: 1) bulging of the annulus into the spinal cord or nerves; 2) narrowing of the space between the vertebra where the nerves exit; 3) tears of the annulus as abnormal loads are transmitted to the annulus and the annulus is subjected to excessive motion between vertebra; and 4) disc herniation or extrusion of the nucleus through complete annular tears.

Current surgical treatments of disc degeneration are destructive. One group of procedures removes the nucleus or a portion of the nucleus; lumbar discectomy falls in this category. A second group of procedures destroy nuclear material; Chymopapin (an enzyme) injection, laser discectomy, and thermal therapy (heat treatment to denature proteins) fall in this category. A third group, spinal fusion procedures either remove the disc or the disc's function by connecting two or more vertebra together with bone. These destructive procedures lead to acceleration of disc degeneration. The first two groups of procedures compromise the treated disc. Fusion procedures transmit additional stress to the adjacent discs. The additional stress results in premature disc degeneration of the adjacent discs.

Prosthetic disc replacement offers many advantages. The prosthetic disc attempts to eliminate a patient's pain while preserving the disc's function. Current prosthetic disc implants, however, either replace the nucleus or the nucleus and the annulus. Both types of current procedures remove the degenerated disc component to allow room for the prosthetic component. Although the use of resilient materials has been proposed, the need remains for further improvements in the way in which prosthetic components are incorporated into the disc space, and in materials to ensure strength and longevity. Such improvements are necessary, since the prosthesis may be subjected to 100,000,000 compression cycles over the life of the implant.

SUMMARY OF THE INVENTION

This invention resides in an artificial disc replacement (ADR) configured for placement between upper and lower vertebrae. The ADR broadly includes a pair of opposing endplate components, each attached to one of the upper and lower vertebrae, a cushioning component disposed between the endplate components; and a filler material contained within the cushioning component. The filler material may be a gas, liquid, foam, or gel, including a hydrogel.

One or both of the endplate components may include a modified surface to increase adherence to the respective vertebral endplates. Such surface modification may include spikes, barbs or other projections, and/or pores or roughening conducive to bony ingrowth. As a further alternative, the modified surface may include one or more projections introduced externally and advanced to penetrate at least a portion of a respective vertebral endplate. According to yet a different option, the modified surface may include deployable projections with retaining rings used to hold the projections together until forced into the vertebrae, at which time the projections spread apart.

In a preferred embodiment, the ADR may further include one or more opposing, spaced-apart projections configured to impinge if the endplate components are subjected to an excessive force. Such projections may allow for unrestricted motion between the endplates until impingement, or may restrict translation between the endplates until a greater excessive force is reached.

DETAILED DESCRIPTION OF THE INVENTION

Figure 1:
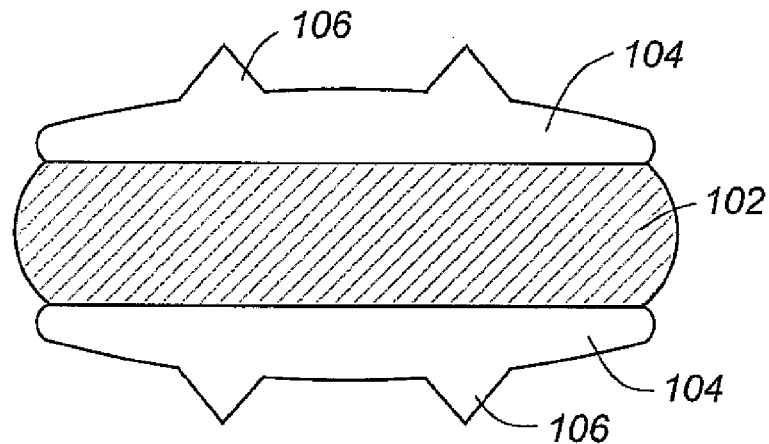
FIG. 1 is a side view drawing of an artificial disc replacement (ADR) according to this invention, including a cushioning component disposed between endplate components.

U.S. Pat. No. 6,419,704 discloses artificial replacements for natural intervertebral discs in humans and animals. Broadly, a shaped body assumes a final volume sized to consume at least a portion of the intervertebral disc space, and a material associated with the shaped body enabling the body to cyclically compress and expand in a manner similar to the disc material being replaced. The body may be composed of a compressible material, such as polymeric urethane or other suitable elastomers, or may include a filling to impart an appropriate level of compressibility. The superior and inferior surfaces may be convex, and may further include grooves, spikes, or other protrusions to maintain the body within the intervertebral space. The body may further be wedge-shaped to help restore or maintain lordosis, particularly if the prosthesis is introduced into the cervical or lumbar regions of the spine.

To enhance strength or longevity, the body may further include the use of fiber-reinforced materials on one or more outer surfaces or wall structures, as the case may be. Similar to commercial tire construction, such fiber-reinforced materials may be of a bias-ply, radial-ply or bias-belted construction. According to one configuration, an artificial disc according to the invention may further include an outer compressible member peripherally attached to a central "hub," similar, at least in concept, to the which a tire is mounted onto a wheel.

The instant invention extends the teachings of the '704 patent through the addition of metal endplates and/or bone-ingrowth surfaces. Although the invention is described in terms of artificial disc replacement (ADR), the approach may also be used to dampen other artificial joints within the body, such as the tibial component of a knee replacement.

As noted in the '704 patent, the ADR may be filled with a gas, liquid, gel (including hydrogels), foam or other compressible material, and the material may be introduced or otherwise provided through the use of a valve, port, syringe, or, alternatively, by way of valveless means. The body in this case is preferably a sealed unit, and may include self-sealing means in the event of a leak or rupture.

If a valve is used to inflate the ADR, it may be configured so as to be accessible during implantation, enabling the surgeon to expand the device in situ. A valve may also be provided in the form of a port enabling subcutaneous post-operative inflation or re-expansion. If a hydrogel is used as the filler material, it may introduced within the body in a dehydrated state prior to implantation, with water being added to expand the material. The liquid may be added through a valve, port or hypodermic in conjunction within a sealed structure or, alternatively, at least a portion of the surface of the body, preferably the superior end or inferior surfaces, may be at least semi-porous. As a further alternative to a valveless structure, one or more reactants may be provided with the body, such that when mixed with one or more other reactants, a gas or foam is generated to expand and fill the body. As yet a further alternative, an ampule or cartridge operative to release a compressed gas or generate a gas, liquid or foam may be activated by an external source of energy such as ultrasound, heat, or other stimuli.

Turning now to the drawings, FIG. 1 is a side view of an ADR according to this invention, wherein a cushioning component 102 is disposed between endplate components 104. In the preferred embodiment, spikes 106 or other projections extend from the endplates to help hold the ADR between the vertebrae.

Figure 2:
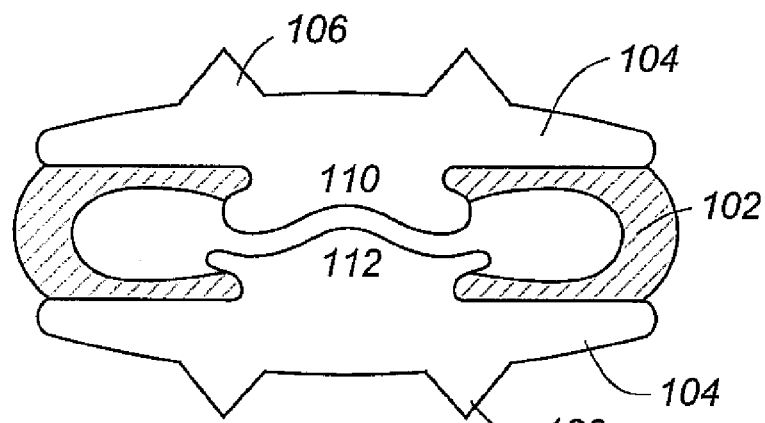
FIG. 2 is a cross section of the device of FIG. 1.

FIG. 2 is a cross section of the device. Note that the endplates 104 have projections 110, 112 that hold and seal the tire-like cushioning component 102. Note further that the projections may be designed to impinge if the ADR is subjected to more than a certain force to protect the cushioning component form excessive pressure. Unless this pressure is reached, however, the metal projections preferably allow unrestricted motion between the endplates until the pressure on the ADR is high enough to force the metal projections together.

Alternatively, metal projections may be used to restrict motion—translation, for example—before enough axial load is applied to the ADR to force the projections together tightly. In either case, when the load on the ADR exceeds a certain amount, for example 350 P.S.I. the metal projections may be used to carry the additional load.

Figure 3:
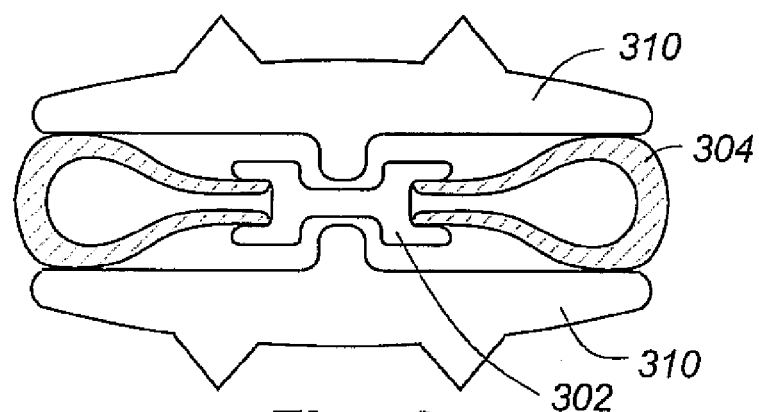
FIG. 3 is a cross section of an alternative embodiment of an ADR according to the invention.

FIG. 3 is a cross section of an alternative embodiment of an ADR according to this invention. In this case a metal hub 302 cooperates with the tire-like component 304 to hold the air, fluid, gel, or other material within the tire. This embodiment is related to FIG. 7 in U.S. Pat. No. 6,419,704. The metal hub 302 may also cooperate with the endplates 310 to limit force on the tire like component.

Figure 4A:
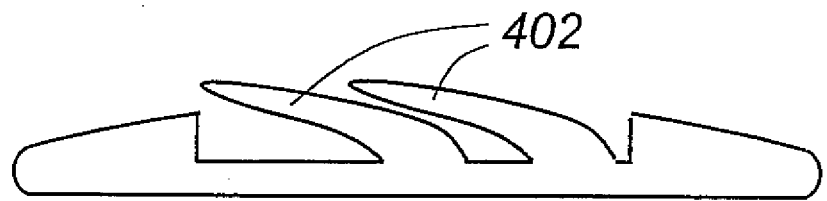
FIG. 4A is a lateral view of an embodiment of the invention with endplates including barbs that help prevent extrusion of the ADR from the vertebrae.
Figure 4B:
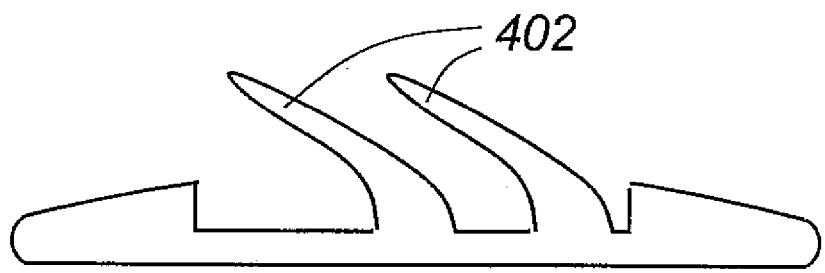
FIG. 4B is a view of the endplate drawn in FIG. 4A with the barbs extended.

FIG. 4A is a lateral view of an embodiment of the invention with endplates including barbs 402 that help prevent extrusion of the ADR from the vertebrae. The barbs bend easily on insertion, but they resist extrusion from the direction of insertion. FIG. 4B is a view of the endplate drawn in FIG. 4A with the barbs extended.

Figure 5A:
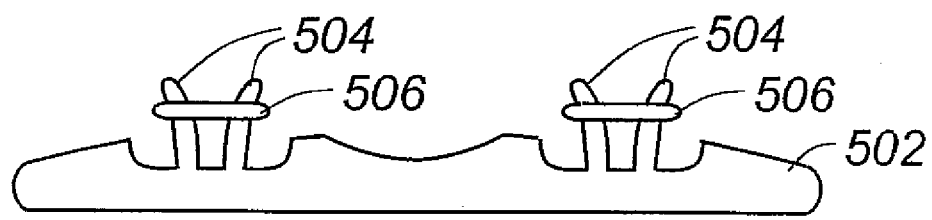
FIG. 5A is a view of the lateral aspect of an endplate with alternative, deployable projections including retaining rings used to hold the projections together.
Figure 5B:
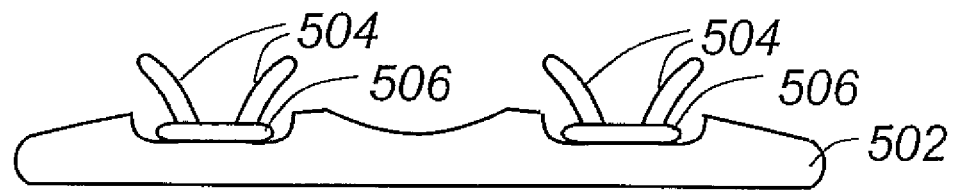
FIG. 5B is a view of the endplate drawn in FIG. 5A with the projections separated.

FIG. 5A is a view of the lateral aspect of an endplate 502 with alternative, deployable projections 504 including retaining rings 506 used to hold the projections 504 together. The ring is forced towards the endplate as the endplate is forced into the vertebra. FIG. 5B is a view of the endplate drawn in FIG. 5A with the projections separated.

Figure 6:
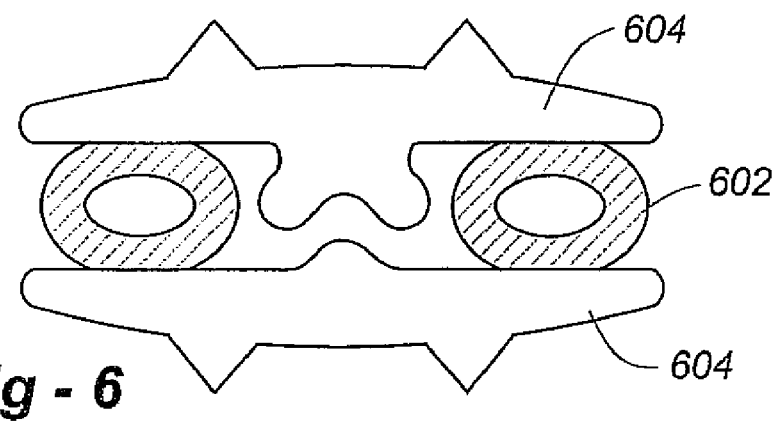
FIG. 6 is a cross section of an alternative embodiment of the device wherein a cushioning component is sealed before it is situated between endplates.
Figure 7A:
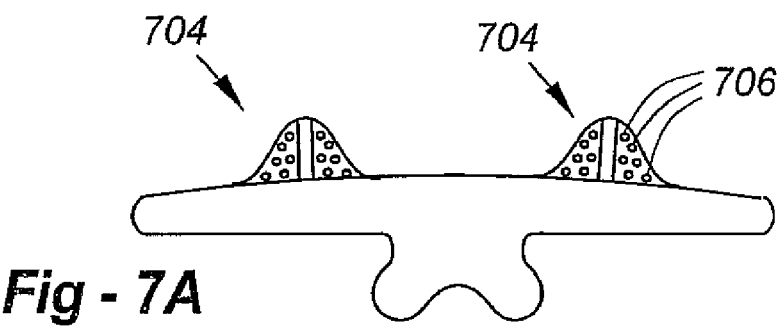
FIG. 7A is a side view of an ADR endplate with alternative projections including a bone-ingrowth surface to better maintain the ADR within the disc space.
Figure 7B:
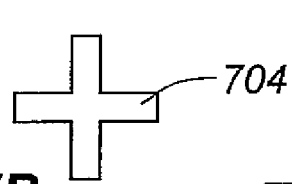
FIG. 7B is a view of the top of one of the projections of FIG. 7A.
Figure 7C:
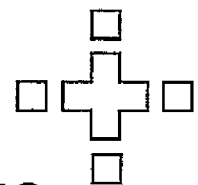
FIG. 7C is a cross-section through the top of one of the projections of FIG. 7A.

FIG. 6 is a cross section of an alternative embodiment of the device wherein the cushioning component 602 is sealed before it is situated between endplates 604. FIG. 7A is a side view of an ADR endplate with alternative projections 704 including a bone-ingrowth surface with holes 706, for example, to allow bone to grow into the projections to better maintain the ADR between the vertebrae. FIG. 7B is a view of the top of one of the projections 704, and FIG. 7C is a cross-section through the top of one of the projections.

Figure 8A:
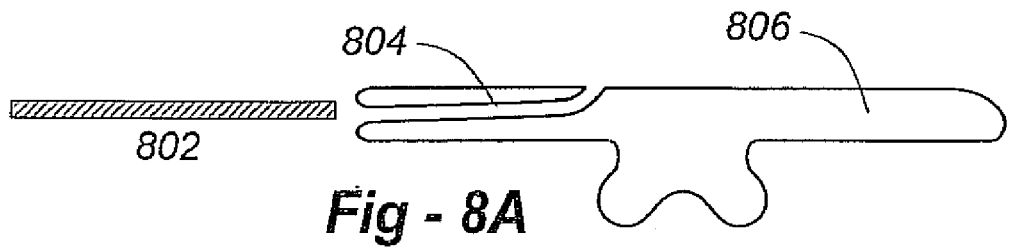
FIG. 8A is a view of an alternative, externally deployable projection according to the invention, wherein a flexible wire or band-like piece is inserted through a hole in the endplate following insertion of the ADR to hold it in position.
Figure 8B:
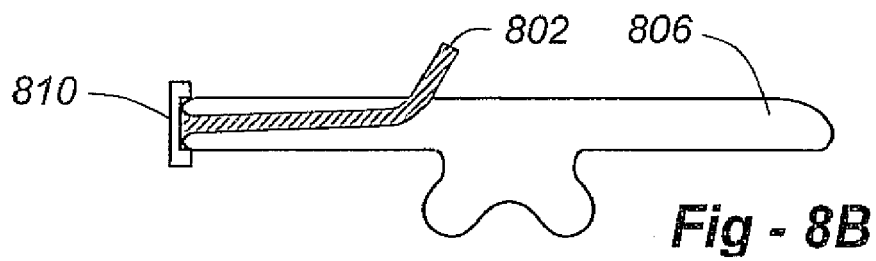
FIG. 8B shows the deployable projection of FIG. 8A in place within the ADR endplate by an optional fastening mechanism.

FIG. 8A is a view of an alternative, externally deployable projection. In this case, a flexible wire or band like piece 802 is inserted through a hole 804 in the endplate 806 following insertion of the ADR. FIG. 8B shows the deployable projection 802 held in place within the ADR endplate by an optional fastening mechanism 810.

In terms of operative procedure, disc replacements according to the invention may be introduced through an anterior, posterior, or lateral approach using an appropriate surgical technique, including open, arthroscopic, laparoscopic, or microscope-assisted procedures. The vertebrae may also be distracted, or the prosthesis may be cooled to ease implantation. More than one ADR according to the invention may be introduced into the same disc space, and may be arranged side-by-side laterally, or anterior to posterior. Separate flaps may be formed in the annulus fibrosis, and one or more bodies may be introduced and inflated, or allowed to expand, to at least partially distract the vertebrae to ease the insertion of additional bodies.

The material of the annulus fibrosis may be reattached to maintain the disc replacement material, or synthetic bands, fabrics, or plates may be added, as required. In the event that multiple prostheses are used within a common disc space, the bodies may include interlocking shapes or structures of varying design to enhance their physical cooperation. In addition, if the replacements are arranged from anterior to posterior, devices more posterior may be smaller or of a lesser "durometer," or those placed anteriorally may be larger or less compressible (or both), again, to enhance an overall lordotic shape. Finally, in all of the embodiments disclosed herein and in the parent applications hereto, septae may be added in the where the air, liquid, or gel is disposed to strengthen the structure.

We claim:

1. An artificial disc replacement (ADR) configured for placement between upper and lower vertebrae, the ADR comprising:
   a pair of opposing endplate components, each attached to a respective one of the upper and lower vertebrae;
   a cushioning component disposed between the endplate components without being attached thereto; and
   a filler material contained within the cushioning component.

2. The ADR of claim 1, wherein the filler material is a gas, liquid, gel or foam.

3. The ADR of claim 1, wherein the filler material is a hydrogel.

4. The ADR of claim 1, wherein one or both of the endplate components include a modified surface to increase adherence to respective vertebral endplates.

5. The ADR of claim 4, wherein the modified surface includes spikes or other projections.

6. The ADR of claim 4, wherein the modified surface includes a projection that may be introduced externally and advanced to penetrate at least a portion of a vertebra.

7. The ADR of claim 4, wherein the modified surface includes barbs that resist extrusion from the direction of insertion.

8. The ADR of claim 4, wherein the modified surface includes deployable projections with retaining rings used to hold the projections together until forced into the vertebrae, at which time the projections spread apart.

9. The ADR of claim 4, wherein the modified surface includes deployable projections with retaining rings used to hold the projections together until forced into the vertebrae, at which time the projections spread apart.

10. The ADR of claim 4, wherein the modified surface is conducive to bony ingrowth.

11. The ADR of claim 1, further including one or more opposing, spaced-apart projections configured to impinge if the endplate components are subjected to an excessive force.

12. The ADR of claim 11, wherein the projections allow unrestricted motion between the endplates until impingement.

13. The ADR of claim 1, wherein the projections restrict translation between the endplates until a greater excessive force is reached.

14. An artificial disc replacement (ADR) configured for placement between upper and lower vertebrae, the ADR comprising:
   a pair of opposing endplate components, each attached to one of the upper and lower vertebrae;
   a cushioning component disposed between the endplate components;
   a filler material contained within the cushioning component; and
   a rounded, centrally located projection on each endplate component configured to impinge if the endplate components are subjected to an excessive force.

15. The ADR of claim 14, wherein the projections allow unrestricted motion between the endplates until impingement.

16. The ADR of claim 14, wherein the projections restrict translation between the endplates until a greater excessive force is reached.

17. The ADR of claim 14, wherein the filler material is a gas, liquid, gel or foam.

18. The ADR of claim 14, wherein the filler material is a hydrogel.

19. The ADR of claim 14, wherein the endplate components include a modified surface to increase adherence to the respective vertebrae.

20. The ADR of claim 19, wherein the modified surface includes spikes or other projections.

21. The ADR of claim 19, wherein the modified surface is conducive to bony ingrowth.

22. The ADR of claim 19, wherein the modified surface includes a projection that may be introduced externally and advanced to penetrate at least a portion of a vertebra.

23. The ADR of claim 19, wherein the modified surface includes barbs that resist extrusion from the direction of insertion.

24. The ADR of claim 19, wherein the modified surface includes deployable projections with retaining rings used to hold the projections together until forced into the vertebrae, at which time the projections spread apart.

25. The ADR of claim 19, wherein the modified surface includes deployable projections with retaining rings used to hold the projections together until forced into the vertebrae, at which time the projections spread apart.

* * * * *

UNITED STATES PATENT AND TRADEMARK OFFICE
CERTIFICATE OF CORRECTION

PATENT NO. : 7,201,776 B2 Page 1 of 1
APPLICATION NO. : 10/303385
DATED : April 10, 2007
INVENTOR(S) : Bret A. Ferree et al.

It is certified that error appears in the above-identified patent and that said Letters Patent is hereby corrected as shown below:

Column 1, line 10, replace, "2000 U.S." with -- 2000, now U.S. --

Column 4, line 17, replace, "to the which" with -- to which --

Column 4, line 63, replace, "form" with -- from --

Column 5, line 66, replace "in the where" with -- in where --

Signed and Sealed this

Sixteenth Day of October, 2007

JON W. DUDAS
*Director of the United States Patent and Trademark Office*